United States Patent
Poulain et al.

(10) Patent No.: US 9,360,470 B2
(45) Date of Patent: Jun. 7, 2016

(54) IN VITRO DIAGNOSTIC METHOD FOR AN INVASIVE FUNGAL INFECTION USING MALDI-TOFF MASS SPECTROMETRY

(71) Applicants: Centre Hospitalier Régional Universitaire de Lille, Lille (FR); Université de Droit et Santé de Lille, Lille (FR); Université Sciences Technologies Lille, Villeneuve d'Ascq (FR); Centre National de la Recherche Scientifique, Paris (FR)

(72) Inventors: Daniel Poulain, Templeuve (FR); Boualem Sendid, Loos (FR); Yann Guerardel, Ronchin (FR); Nadine Francois, Lille (FR)

(73) Assignees: Centre Hospitalier Regional Universitaire De Lille, Lille (FR); Universite De Droit Et Sante De Lille, Lille (FR); Universite Sciences Technologies Lille, Villeneuve d'Ascq (FR); Centre National De La Recherche Scientifique, Paris (FR)

( * ) Notice: Subject to any disclaimer, the term of this patent is extended or adjusted under 35 U.S.C. 154(b) by 0 days.

(21) Appl. No.: 14/410,525

(22) PCT Filed: Jun. 24, 2013

(86) PCT No.: PCT/FR2013/000158
§ 371 (c)(1),
(2) Date: Dec. 22, 2014

(87) PCT Pub. No.: WO2014/001658
PCT Pub. Date: Jan. 3, 2014

(65) Prior Publication Data
US 2015/0338391 A1    Nov. 26, 2015

(30) Foreign Application Priority Data
Jun. 26, 2012 (FR) .................................. 12/01796

(51) Int. Cl.
*G01N 33/50* (2006.01)
*G01N 30/00* (2006.01)
*G01N 33/52* (2006.01)

(52) U.S. Cl.
CPC ............ *G01N 33/50* (2013.01); *G01N 33/5002* (2013.01); *G01N 33/52* (2013.01); *G01N 2333/40* (2013.01); *G01N 2400/12* (2013.01); *G01N 2560/00* (2013.01); *G01N 2800/26* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 8,491,791 B2 * | 7/2013 | Lomas ................... | B01J 20/286 137/571 |
| 2010/0003699 A1 | 1/2010 | Satomaa et al. | |
| 2012/0100543 A1 | 4/2012 | Sampath et al. | |

FOREIGN PATENT DOCUMENTS

| | | |
|---|---|---|
| EP | 1876441 A1 | 1/2008 |
| WO | 2005111627 A2 | 11/2005 |
| WO | WO 2005/111627 A2 | 11/2005 |

OTHER PUBLICATIONS

Qian, Jiang et al.; "MALDI-TOF mass signatures for differentiation of yeast species, strain grouping and monitoring of morphogenesis markers"; Anal. Bioanal. Chem; 2008; vol. 392, pp. 439-449.

Ha, Miyoung et al.; "Development of a Matrix-prespotted Plate for Enhancing the Reproducibility of Serum Glycan Analysis by MALDI-TOF-MS"; Mass Spectrometry Letters; 2011; vol. 2, No. 3, pp. 61-64.

Fiedler, Georg et al.; "Standardized Peptidome Profiling of Human Urine by Magnetic Bead Separation and Matrix-Assisted Laser Desorption/Ionization Time-of-Flight Mass Spectrometry"; Clinical Chemistry; 2007, vol. 53, No. 3, pp. 421-428.

Whistler, Roy, et al.; "Chromatographic Separation of Sugars on Charcoal"; Journal of The American Chemical Society, Feb. 1950, vol. 72, No. 2, pp. 677-679.

Welham, Kevin J., et al. "The characterization of micro-organisms by matrix-assisted laser desorption/ionization time-of-flight mass spectrometry." Rapid Communications in Mass Spectrometry 124 (1998): 176-180.

Duffy, B. "MALDI-TOF mass spectrometry: Applications for rapid bacterial identification and phylogenetic analysis." Phytopathology 101 (2011): S145.

(Continued)

*Primary Examiner* — Padma V Baskar
(74) *Attorney, Agent, or Firm* — Ostrolenk Faber LLP (57) ABSTRACT

A method for the in vitro diagnosis of an invasive fungal infection by MALDI-TOF mass spectrometry. The method involves, providing a liquid biological sample from a mammal, said biological sample containing, in particular, proteins and/or lipids and/or salts and/or polysaccharides and/or oligosaccharides and/or monosaccharides capable of forming complexes with said proteins and/or lipids and/or salts; treating said sample with biological liquid so as to extract said polysaccharides and/or oligosaccharides and/or monosaccharides; determining, by MALDI-TOF mass spectrometry, whether or not there is present among said extracted polysaccharides, oligosaccharides and/or monosaccharides, at least one given compound of interest coming from said fungal microorganism and chosen from polysaccharides, oligosaccharides and monosaccharides; and deducing, if said given compound of interest is present in said sample, that said mammal is suffering from an invasive fungal infection.

19 Claims, 2 Drawing Sheets

(56) References Cited

OTHER PUBLICATIONS

Elosta, Shaban, et al. "MALDI TOF mass spectrometry of selected mycotoxins in barley." J. Appl. Biomed 5 (2007): 39-47.
Konrad, R., et al. "Matrix-assisted laser desorption/ionisation time-of-flight (MALDI-TOF) mass spectrometry as a tool or rapid diagnosis of potentially toxigenic Corynebacterium species in the laboratory management of diphtheria-associated bacteria." Euro Surveill 15.43 (2010): 1-5.
Risch, Martin, et al., "Comparison of MALDI TOF with conventional identification of clinically relevant bacteria." Swiss Med Wkly 140 (2010): w13095.
Ellepola, A. N., and Christine J. Morrison. "Laboratory diagnosis of invasive candidiasis." J Microbiol 43.5 (2005): 65-84.
Marcos, Javier Yugueros, and David H. Pincus. "Fungal diagnostics: review of commercially available methods." Fungal Diagnostics. Humana Press, 2013. 25-54.
Willinger, Birgit, et al. "Comparison of a new commercial test, GLABRATA RTT, with a dipstick test for rapid identification of Candida glabrata." Journal of clinical microbiology 43.1 (2005): 499-501.
Freydiere, A. M., et al. "Routine use of a commercial test, GLABRATA RTT, for rapid identification of Candida glabrata in six laboratories." Journal of clinical microbiology 42.10 (2004): 4870-4872.
Freydiere, A-M., et al. "Rapid identification of Candida glabrata with a new commercial test, GLABRATA RTT." Journal of clinical microbiology 41.8 (2003): 3861-3863.
Kumar, M. K., et al. "Characterization of bacteriophages PT21 and UASP infecting Ralstonia solanacearum: A potential bio-control agent." Phytopathology. vol. 101. No. 6.3340 Pilot Knob Road, St Paul, MN 55121 USA: Amer Phytopathological Soc, 2011.
Wang, Cui-hong, et al. "High-sensitivity matrix-assisted laser desorption/ionization Fourier transform mass spectrometry analyses of small carbohydrates and amino acids using oxidized carbon nanotubes prepared by chemical vapor deposition as matrix." Analytica chimica acta 604.2 (2007): 158-164.
Broberg, Susanna. Studies of oligo-and polysaccharides by MALDI-TOF and ESI-ITMSn mass spectrometry. vol. 452. 2004.
Kailemia, Muchena J., et al. "Oligosaccharide analysis by mass spectrometry: a review of recent developments." Analytical chemistry 86.1 (2013): 196-212.
Harvey, David J. "Analysis of carbohydrates and glycoconjugates by matrix-assisted laser desorption/ionization mass spectrometry: An update for the period 2005-2006." Mass spectrometry reviews 30.1 (2011): 1-100.
Harvey, David J. "Analysis of carbohydrates and glycoconjugates by matrix-assisted laser desorption/ionization mass spectrometry: An update for 2009-2010." Mass spectrometry reviews 34.3 (2015): 268-422.
Harvey, "Mass Spectrometry: Matrix-Assisted Laser Desorption/Ionization"; Reference Module in Chemistry, Molecular Sciences and Chemical Engineering; http://dx.doi.org/10.1016/B978-0-12-409547-2.00323-1; 2013.
Dhiman, Neelam, et al. "Performance and cost analysis of matrix-assisted laser desorption ionization—time of flight mass spectrometry for routine identification of yeast." Journal of clinical microbiology 49A (2011): 1614-1616.
Arendrup, M. C., et al. "ECIL-3 classical diagnostic procedures for the diagnosis of invasive fungal diseases in patients with leukaemia." Bone marrow transplantation 47.8 (2012): 1030-1045.
Harvey, David J. "Matrix-assisted laser desorption/ionization mass spectrometry of carbohydrates." Mass Spectrometry Reviews 18.6 (1999): 349-450.
Richard K.T. Kam, et al., "High-Throughout Quantitative Profiling of Serum N-Glycome by MALDI-TOF Mass Spectrometry and N-Glycomic Fnigerprint of Liver Fibrosis", Clinica Chemistry 53:7, 1254-1263, 2007 (10 pages).
An, Hyun Joo, et al. "Profiling of glycans in serum for the discovery of potential biomarkers for ovarian cancer." Journal of proteome research 5.7 (2006): 1626-1635.
Ha, Miyoung, et al. "Development of a Matrix-prespotted Plate for Enhancing the Reproducibility of Serum Glycan Analysis by MALDI-TOF-MS." Mass Spectrometry Letters 2.3 (2011): 61.
Ho, Yen-Peng, and P. Muralidhar Reddy. "Advances in mass spectrometry for the identification of pathogens." Mass spectrometry reviews 30.6 (2011): 1203-1224.
Qian, Jiang, et al. "MALDI-TOF mass signatures for differentiation of yeast species, strain grouping and monitoring of morphogenesis markers." Analytical and bioanalytical chemistry 392.3 (2008): 439-449.

\* cited by examiner

IN VITRO DIAGNOSTIC METHOD FOR AN INVASIVE FUNGAL INFECTION USING MALDI-TOFF MASS SPECTROMETRY

CROSS REFERENCE TO RELATED APPLICATIONS

The present application is a 35 U.S.C. §371 National Phase conversion of PCT/FR2013/000158, filed Jun. 24, 2013, which claims benefit of French Application No. 12/01796, filed Jun. 26, 2012, the disclosure of which is incorporated herein by reference. The PCT International Application was published in the French language.

TECHNICAL FIELD OF THE INVENTION

The present invention relates to an in vitro diagnostic method for an invasive fungal infection using MALDI-TOF spectrometry. The invention method can also quantify a compound of interest contained in the sample and used as a marker for the diagnosis of an invasive fungal infection.

BACKGROUND OF THE INVENTION

Yeasts such as *C. albicans* are often present in the mucosa of healthy people in whom they usually cause no specific disease or symptom. When the body is weakened, the yeasts proliferate and pass into the blood system, in which case reference is made to invasive or systemic infection. In the case of *C. albicans,* 40% of candidaemias (fungaemias caused by *C. albicans*) are fatal in human beings. Invasive fungal diseases (IFD) or invasive fungal infections are common, serious hospital disorders. Despite effective treatments, the costs of which are increasingly difficult for hospitals to carry, the morbidity of the IFD is not falling. Conventional mycology methods (isolation/identification) are often defective as risk-free access to the localised sites of infection in the patient for sampling the fungus is often impossible. Blood cultures are also negative in almost half of cases of IFD. So-called molecular biology methods (PCR) do not resolve these problems. In addition, it has now been established that early introduction of anti-fungal treatment—based on a diagnosis—influences patients' survival. Amongst the additional or alternative diagnostic methods to conventional mycology, the use of detection methods for circulating glycans (i.e. fungal glycans contained in the serum of infected patients) in patient sera is now recognised by clinicians. These glycans come from the wall of the microcetes or their precursors and can be detected with commercial immunological tests. As such, the Platélia® *Candida* Antigen test can detect mannans and galactamannans originating from *Candida* and *Aspergillus* respectively. Biochemical kits such as those marketed under the brand Fungitell®, for example, can detect glucans, which are common to *candida* and *Aspergillus.*

Each of the two types of "kit" listed above contains many different reagents and internal standards. The need to construct calibration curves into each batch leads to increased consumption of reagents, particularly when intended to test serum. This need for calibration can sometimes lead to investigations not being performed for financial reasons (because of insufficient reagents). It is, for example, difficult with Fungitell®, to justify the use of nine wells for calibration and to monopolise a technician for half a day to test one serum. These tests also require access to specifically programmed autoanalysers and have interfaces with the informatics system, which further complicates their urgent practical uses on a single patient basis, when they should be able to respond to a request for them as soon as possible.

All of these tests are therefore particularly demanding in terms of time or reagents. In addition, they produce a certain number of false positive results which interfere with the diagnosis. This is particularly true for biochemical measurement of glucan(s) which are interfered with by the presence of haemoglobin (sera which are haemolysed when collected) or the frequent metabolic abnormalities in patients at risk of IFD, such as hypertriglyceridaemia, or the presence of bilirubin or hypoproteinaemia.

Finally, false positive results in patients hospitalised in intensive care with multiple infections with organisms other than fungi has been reported on several occasions. The type of mechanisms in false positive reactions in detecting the P-D-glucans is still unknown as the substances which circulate in these patients' sera have not been characterised on a molecular basis. Because of the existence of these false positive results, some patients who would not require any treatment are given antifungal antibiotic therapy, which prolongs their hospital stay. In the case of false negative results, which are also seen, the interpretation is made that the infection is not fungal but bacterial, and the patient is given antibacterial antibiotic therapy, which is harmful and may be fatal.

In addition, the Fungitell® kit uses blood from the limulus, an animal which is beginning to become rare and at present, it is not possible to farm limuli. They are therefore captured in their natural environment. A sample of blood is taken from the limuli before they are releasing, and 20% of the limuli which are released do not survive.

SUMMARY OF THE INVENTION

One aim of the present invention is to propose a new in vitro diagnostic method for an invasive fungal infection.

Another aim is to propose an in vitro method as described above which is more reliable and in particular a method which will help to avoid false negative and false positive results as described above.

The present invention relates to an in vitro method for invasive fungal infection caused by a pathogenic fungal microorganism, according to which, characteristically:

polysaccharides and/or oligosaccharides and/or monosaccharides contained in a sample of a biological liquid obtained from a mammal are extracted, said biological liquid containing in particular, proteins and/or lipids and/or salts and/or polysaccharides and/or oligosaccharides and/or monosaccharides which are liable to form complexes with said proteins and/or lipids and/or salts using MALDI-TOF mass spectrometry to establish the presence or absence amongst the extracted polysaccharides, oligosaccharides and/or monosaccharides, of at least one given compound of interest originating from said fungal microorganism and selected from the polysaccharides, oligosaccharides and monosaccharides.

concluding that if said given compound of interest is present in said sample, said mammal is suffering from an invasive fungal infection.

One merit of the inventors is therefore to have been able to show that it is possible with MALDI-TOF mass spectrometry to detect in a complex biological liquid the presence of a compound selected from amongst sugars in particular, polysaccharides, oligosaccharides and monosaccharides which originate from the pathogenic microorganism and not from the host mammal. Another merit of the inventors is to have shown that this compound of interest is a marker for the diagnosis of invasive fungal inventions. The presence of a compound of interest (marker) is represented by a visible peak on the spectrum obtained by MALDI-TOF mass spectrometry. It was not evident that a compound such as the above described originating from a pathogenic fungal microorganism may be detected by MALDI-TOF mass spectrometry in a biological liquid. It was even less evident that this compound of interest could indicate an invasive fungal infection. It could be thought that the amount of compound of interest present could be too small in order to be detected or that the signal representing this compound of interest would be hidden amongst the thousands of signals which may be seen in a biological liquid, particularly serum. Furthermore, sugars (polysaccharides, oligosaccharides and monosaccharides) form complexes with lipids, proteins and salts in biological liquids and are therefore difficult to detect. The significant peak or peaks representing one of the compounds of interest used to diagnose an invasive fungal infection caused by a given microorganism are firstly identified by, for example, reproducing the experimental protocol described in this present application with samples of biological liquid originating from mammals infected with the given pathogenic fungal microorganism(s). The invention method can detect compounds of interest as listed above without the need to label them.

It is possible according to the invention method to use MALDI-TOF mass spectrometry to detect the simultaneous presence of several compounds of interest, one of which belongs to the group of polysaccharides, oligosaccharides or monosaccharides. All of the compounds of interest can also, according to the invention, be sugars as described above.

Advantageously, in order to extract said compound of interest,
  complexes contained in said sample of biological liquid are dissociated by precipitation/coagulation of the majority of said proteins or said lipids
  said sample is centrifuged and the supernatant is separated from the solid fraction;
  supernatant is recovered.
  said compound of interest contained in the supernatant is separated from any residual proteins and any residual lipids notably by reverse phase chromatography and said compound of interest is separated from said salts particularly by absorption chromatography.

According to the invention, it is possible firstly to separate the compound of interest from the salts and then to separate it from any residual proteins and/or residual lipids or to perform the stages in reverse order.

Advantageously, in order to dissociate said complexes a complexing agent is added to said sample, particularly a base, and in particular EDTA, and said mixture obtained is heated to boiling and in particular to a temperature of 100° C. or over and 140° C. or less and specifically to close to 120° C. The heating time may be adjusted by the Man skilled in the Art according to the sample size, technique used for heating and recipient containing the sample. The whole volume of the sample must be brought to boiling. The heating time is adjusted in order not to degrade the sample, particularly the sugars which it contains. As an example, the heating time is between three minutes and seven minutes. The invention method is particularly robust and extremely inexpensive in terms of reagents. In terms of analytical compatibility, the technical time is no greater than the time required to use existing kits. The complexing agent such as EDTA combined with heating can dissociate the complexes which exist in said biological liquid. The complexing agent can in particular release sugars from lectins which are dependent on divalent cations.

According to a particular method of use, reverse phase chromatography is applied first, followed by absorption chromatography.

Advantageously, a column containing a hydrophobic phase is used for reverse phase chromatography and a column containing active charcoal for the absorption chromatography.

The hydrophobic column may be a column filled with any solid support onto which is bonded, for example, onto octadecyl groups (C18). The support may be a polymer or porous silica. The size and volume of these columns will vary depending on the volume of serum to be processed. The column containing active charcoal may contain an equal weight of active charcoal and Célite (diatomised earth) which enables mono- and disaccharides to be recovered in the eluate, the other saccharides being retained in the column.

The size and molecular mass of the compound of interest are not limited according to the invention. The compound of interest may for example have an m/z ratio of under 1000. The compound of interest may be a disaccharide, in particular a hexose dimer representing an m/z signal=365. This compound of interest, which is a marker of invasive fungal infection, may for example be trehalose.

Advantageously, after addition of said complexing agent, at least one enzyme capable of degrading the polysaccharides and/or oligosaccharides is added and chemical treatment is applied in order to cleave said polysaccharide and/or oligosaccharide chains, with the result that the amount of said compound of interest is potentially increased. The use of endomanosidase can free oligomanosides in order to increase the intensify of their mass spectrometry (MALDI-TOF) signals. Chemical treatments such as acetolysis can also be considered in this situation. It is also possible to work in a similar way on the galactomannans, glucans and even chitin (three predominant compounds in the fungal wall) in order to release short chains from these polymers.

Thus, an increase in signal intensity from a trisaccharide after mannosidase allows the signal to be attributed to circulating mannans.

This analytical process may be supplemented by the action of exoglycosidases, the conclusions on which are based conversely on disappearance of the signal. The pathogen involved can therefore be established according to the type of oligosaccharides present in the sample of biological liquid.

Advantageously, said compound of interest is selected from amongst the following mono- and oligosaccharides. [N-acetyl-glucosamine $\beta(1,4)$ N-acetyl-glucosamine]$_n$, wherein n is a number of one or above and below 10 or equal to 10, oligosaccharides comprising 2 to 10 monosaccharides, particularly hexose oligomers, in particular, hexose dimers, glucans, notably glucans of the type [$\beta(1,3)$ glucose, glucose]$_n$, [$\beta$-(1,6) glucose, glucose]$_n$ wherein n is a number of one or more and below 10 or equal to 10, mannans, notably mannans of the type [$\alpha$-(1,2) mannose, mannose]$_n$, [$\alpha$-(1,3) mannose, mannose]$_n$, [$\alpha$-(1,6) mannose, mannose]$_n$, [$\beta$-(1,2) mannose, mannose]$_n$ where n is a number of 1 or more and below 10 or equal to 10, galactomannans, galactans, arabinogalactans and glucuronoxylomannans.

According to a particular method of use of the invention, the compound of interest is a compound produced by the pathogenic fungal micro-organism, more specifically, trehalose.

The compound of interest used as a marker may be a hexose dimer, particularly trehalose (m/z=365). Such a type of compound of interest has been found to be a good marker of infection with a pathogen, particularly an infection with *Candida albicans*.

The pathogenic fungal microorganism may be selected from the pathogenic fungal microorganisms capable of producing trehalose in response to the action of said mammalian immune system, *Candida* spp, particularly *Candida albicans*, *Aspergillus* spp., *Fusarium* spp., *Trichosporon* spp., *Saccharomyces cerevisiae*, *Acremonium* spp., *Coccidioides immitis*, *Histoplasma capsulatum*, *Sporothrix schenckii* and *Pneumocystis jirovecii*.

Advantageously, the pathogenic fungal microorganism is selected from amongst the above listed pathogenic fungal microorganisms which produce trehalose in response to the action of the mammalian immune system.

Advantageously, a known amount of at least one standard compound is added to said sample in order that by comparing the intensity of the signal obtained for said given compound of interest with the signal obtained for said standard compound, the amount of said compound of interest contained in said sample can be established. The compound may be added to the sample before it is processed; it is possible according to the invention to use as a standard compound, compounds with m/z values close to that of the oligosaccharides being analysed. It is considered that when m/z values belong to an interval (m/z of the compound of interest −5; m/z of the compound of interest +5) or at the limits of this interval are similar to the m/z value of the compound of interest.

Advantageously, the standard compound behaves chromographically on the columns used identically to the behaviour of the compound to be detected. It may in this case be added after the heating stage and before passing through the two columns. The standard column must not be a compound present in biological liquids whether healthy or pathological. The standard column must not be liable to be identified as arising from microbial contaminations. Advantageously for these purposes, disaccharides or trisaccharides possibly labelled with a radio isotope are used. The deuterated trehalose (MW 2H trehalose=356+Na=379) may, for example, be used as a standard compound.

According to another operational method, the ratio of signal intensity of the signal from the given compound of interest to the intensity of a ubiquitous endogenous signal is determined, said endogenous signal being previously identified and possibly specific to the type of biological liquid from which the sample has been obtained, with the result that said given compound of interest contained in said sample can be quantified.

This is in fact another merit of the inventors to have identified a constant signal (said to be a ubiquitous signal) present in all serum samples which may be used to quantify the compound of interest in the type of biological liquid. The Man skilled in the Art may easily identify a ubiquitous signal by carrying out the MALDI-TOF analysis on several samples (preferably not infected or not suspected to be infected) of a given type of biological liquid. The ubiquitous signal is a constant signal found in all samples of this type of liquid and the intensity of the signal as described above represents the height of the peak which appears on the spectrogram obtained from MALDI-TOF analysis.

Therefore, according to the invention, the biological liquid may be selected from arterial or venous blood, serum, liquids from the genital mucosa, respiratory tract liquids, particularly liquids obtained from bronchoalveolar lavage, bronchial aspiration, tracheal aspiration, expectoration, sputum, liquids which have been used to collect skin and integument, effusion liquids, liquids from closed cavities, particularly cerebrospinal liquid, liquids from the gastro-intestinal or urinary tract and liquids obtained from grinding a biopsy fragment.

The present invention also concerns a kit enabling the method of the invention. According to one embodiment, it comprises
  at least an initial support consisting of a solid hydrophobic phase enabling reverse phase chromatography to be carried out;
  at least a second container comprising an input opening, an output opening and containing a filling of powdered active charcoal arranged between said input opening and said output opening.

The filling may be prepared by mixing an equal amount of commercial activated charcoal Célite® (diatomised earth) according to a principle well known by the Man skilled in the Art and described in the following publication: Whistler and Durso, Journal of American Chemical Society, 1950.

The solid hydrophobic phase may exist in divided form and comprise a magnetic material, such that it possible to remove the solid phase with a magnet following contact with said biological liquid. For example, the solid hydrophobic phase may be in the form of multiple beads containing a ferrous or magnetic material and covered with a hydrophobic material. The solid hydrophobic phase in divided form is placed in contact with the sample of biological liquid. They may be mixed. The beads offer a large contact surface area. After a certain contact time the solid hydrophobic phase is removed with a magnet, by for example immersing the magnet in the mixture of biological liquid and beads of solid hydrophobic phase. The beads adhere to the magnet, which enables the processed biological liquid to be separated easily.

According to another operational method, the kit also contains a given amount of a standard compound selected from amongst the monosaccharides, disaccharides and the trisaccharides possibly labelled with a radioactive isotope, notably deuterated trehalose.

Advantageously, the kit may also contain a given amount of an enzyme able to react with the complexes formed by the polysaccharides and/or oligosaccharides and/or monosaccharides contained in a biological liquid.

The support containing a solid hydrophobic phase enabling the aforementioned reverse phase chromatography to be applied may be a plate, a well, a column, a tube or a plate containing a large number of wells.

The container for the solid active charcoal filling may be wells, a column, a tube or a plate containing many wells independently of the choice of aforementioned support. Advantageously, the kit according to the invention also contains a MALDI plate.

The present invention also involves the use of a compound of interest selected from amongst the polysaccharides, the oligosaccharides and the monosaccharides, in particular trehalose for the in vitro diagnosis of an invasive fungal infection by MALDI-TOF mass spectrometry.

BRIEF DESCRIPTION OF THE DRAWINGS

The present invention, its characteristics, particular features and the various advantages which it provides will appear more clearly on reading the description which follows and which refers to a specific operational method shown as a non-exhaustive example and referring to the appendiced designs, amongst which.

DESCRIPTION OF PREFERRED EMBODIMENTS

Definitions

According to the invention, the mammal is not limited: it may be a human being or any other mammal. The present invention therefore has applications in human medicine and veterinary medicine.

According to the invention, the oligosaccharides and the polysaccharides are defined as being monosaccharides linked to each other with glycoside bonds. The oligosaccharides are made up of 2 to 10 monosaccharides and the polysaccharides are made up of more than 10 monosaccharides.

A MALDI-TOF spectrometer is a mass spectrometer in which a MALDI matrix assisted laser desorption/ionisation is coupled to a TOF (Time of Flight) mass spectrometer) analyser. This type of instrument is apparently relatively widely available, including in the hospital environment.

According to the invention, the presence of the compound of interest is defined by the presence of the peak visible on the mass spectrum obtained by MALDI-TOF spectrometry. The Man skilled in the Art is also able to recognise on such a spectrum the presence of a peak visible and therefore significant peak. In particular, a significant peak may according to the invention represent a peak of 1% or more; Advantageously a 3% or more and more Advantageously at least equal to almost 5% of the intensity of a reference peak.

According to the invention, the term "invasive fungal infection" groups together those infections which arise from the presence of yeast (mushrooms) in peripheral mammal blood and infections which cause injury to the blood and at least one tissue. In the case of, for example and infection with *C. albicans*, in which liver and renal injury may take place which arises from extravascular haematogenous spread of yeast, the term "invasive fungal infection" groups together candidaemia and invasive candidiasis.

According to the invention, the presence of the compound of interest is defined by the presence of the peak visible on the mass spectrum obtained by MALDI-TOF spectrometry. The Man skilled in the Art is also able to recognise on such a spectrum the presence of a peak visible and therefore significant peak. In particular, a significant peak may according to the invention represent a peak of 1% or more; Advantageously a 3% or more and more Advantageously at least equal to almost 5% of the intensity of a reference peak.

According to the invention, the term "invasive fungal infection" groups together those infections which arise from the presence of yeast (mushrooms) in peripheral mammal blood and infections which cause injury to the blood and at least one tissue. In the case of, for example and infection with *C. albicans*, in which liver and renal injury may take place which arises from haematogenous extra-vascular spread of yeast, the term "invasive fungal infection" groups together candidaemia and invasive candidiasis.

According to the invention, a compound originating from a pathogenic fungal micro-organism as being any residual substance from a pathogenic microorganism present in host biological liquids, released either spontaneously or as a result of depolymerisation/degradation by the microorganism, itself or by host enzymes. The compound of interest may originate from polysaccharides or glycan couples of glycoproteins or glycolipids originating from the pathogenic fungal microorganisms. The compound of interest may originate from the wall of the pathogenic fungal microorganism or be the degradation product of the wall, a compound secreted/excreted by the pathogenic fungal microorganism or expressed by it and released when said microorganism is destroyed by the host cells. It may be a compound which originates from an interaction between the infected mammalian system and said pathogenic fungal microorganism.

The term pathogenic fungal microorganism is intended to mean fungi (yeasts), the genetic machinery of which enables polysaccharide or oligosaccharide sequences which differ from those produced by mammals, or to produce these in amounts which are not physiologically present in their bodies. According to the invention, the terms "biological liquid" refer to any liquid originating from a living organism, particularly a mammal, and more specifically a human being, and containing water, at least one type of protein and/or one type of liquid and/or at least one type of mineral salt, present in the form of an ion such as for example, sodium or potassium, the ion possibly being metallic. In the terms of the present invention, a salt is defined as being a mineral salt in the form of an ion.

The experiments described below, referring to a fungal infection caused by *C. albicans* may be produced with mammals artificially infected by one, two or more pathogenic fungal microorganisms studied. The experiments below can then be used to establish the compound or compounds of interest suitable for using as a marker of the invasive fungal infection caused by the pathogenic microorganism(s) to be studied, characterised said compound or compounds of interest and establish it/their relationship with the infection.

EXPERIMENTAL PART

First Stage

Processing of biological samples to detect the glycans the procedure applied to sera.
  Add 300 pL of test sample to 1.5 ml sterile micro tubes and 100 µL of treatment solution (EDTA acid solution) into each tube "Vortex" mix Place the hermetically sealed micro tubes with interlock jumps for 6 min at 120° C. on a heating block Remove the tubes and centrifuge them for 10 min at 10,000 g The supernatant (150 μl) is transferred into a 1.5 ml sterile micro tube Subsequent processing to detect glycans by mass spectrometry is carried out on the supernatant. This process releases/dissociates the mannans and galactomannans of protein complexes which are coagulated in the clot and in no way changes the colorimetric measurement of the glucan (Fungitell® kit) which produces results consistent with those from the same unprocessed sample. Conversely, this processing removes interferences due to excess proteins, triglycerides, bilirubin and/or haemoglobin.

Second Stage

Processing of supernatants to purify and concentrate the oligosaccharides prior to mass spectrometry.

100 μL of supernatant are placed on a solid phase extraction (SPE) cartridge (ref SPE-C18: C18 Sep-Pak cartridge (Waters)) (1 volume)), (one column with hydrophobic filling) which has been preconditioned with five volumes of a solution of acetonitrile (ANC) and water (75:25, vol/vol) and washed with 10 volumes of water. After the volume of supernatant collected has entered the cartridge the cartridge is rinsed with two volumes of water which are collected. The C18 column eluate is placed on an SPE cartridge containing a mixture of equal weights of commercial activated charcoal and Célite® (equivalent volume) which has been preconditioned with five volumes of a solution on ANC/$H_2O$ (25:75, vol/vol) and then rinse with 10 volumes of water. After the volume of supernatant has passed into the cartridge, the cartridge is rinsed with 20 volumes of water and the eluate is discarded. The column is rinsed with two volumes of a solution of ANC/$H_2O$ (25:75, vol/vol). The first hundred μL are rejected and the next two hundred μL are collected. The eluate (ANC/$H_2O$) is dried.

Third Stage

Analysis of Oligosaccharides by Mass Spectrometry.

The mass spectrometry used is a MALDI-TOF Voyager Elite DES-TR spectrophotometer (Perspective Biosystems Framingham, Mass.). The dry extract is dissolved in water and 1 pL solution is spiked with 1 μL of a solution of dihydrobenzoic solution (10 mg/ml in ACN/$H_2O$ 50/50). 1 μL of the solution is deposited on a MALDI-TOF plate (applied by stainless steel plate, 96 wells, hooped) and crystallised at 50° C. The MALDI-TOF analysis is performed in positive reflectron mode, the reflectron mode, using acquisition parameters optimised from neutral oligosaccharides with an m/z ratio of under 1,000. Following data acquisition, the presence of oligoglucans in the mixture is determined by observing the adducts (M+Na)+ generated. The masses (M) of interest for the diagnosis are calculated according to the equation M $Hex_n$=180+[162](n−1)+23. Relative quantification of the molecular groups is performed by calculating the ratio of the M $Hex_n$ signals i.e. an ubiquitous endogenous signal or with an external standard added to the sample in the first phase of the second stage. To date, the signal which is of interest for the diagnosis is M Hex2=365. Examples of analyses shown further on in the text are based on calculation of the ratio of the 365/361 signals.

Analysis of Human Sera

The invention method was applied to 12 sera from patients hospitalised at the Lille Regional University Hospital and selected based on the following criteria:

i) Patients who had developed systemic candidiasis during their hospitalisation, proven by at least one *C. albicans* blood culture ii) Patients for whom a detection of blood glucan or mannan test had been requested which was positive for one or both, and which had guided or confirmed the diagnosis on a serum sample taken in the week before or within two weeks after the blood culture sample was found to be positive iii) Availability of a minimum volume of 1 ml of residual serum stored at −20° C. for one year for legal reasons Table I below summarises the results obtained using the Platélia® antigen and Fongitell® kits on the 12 patients' sera which met the above criteria and were therefore suffering from IFD. Serum sample mannans as detected by the Platélia®, glucans as detected by the Fongitell® test.

TABLE I

| Serum Sample | Mannans as detected by Platélia Candida antigen ® (pg/mL) | Glucans as detected by the Fungitell ® test (pg/mL) |
|---|---|---|
| G3 |  | 11 |
| G4 | 0 | 0 |
| G5 |  | 62 |
| G6 |  | 11 |
| G10 | >500 | 126 |
| G12 | 0 | 178 |
| G15 | 0 | 0 |
| G21 | 216 | 232 |
| G25 | 610 | 43 |
| G32 | 0 | >500 |
| G42 |  | 1272 |
| G49 | >500 | 388 |

The method according to the invention was applied to the above sera samples. The results can be seen on FIGS. 1a-1d and 2a-2c. As shown on FIGS. 1a-1d MALDI plate analysis performed on sera G25, G32, G42 and G49 in table I to which the invention method was applied show firstly a high intensity signal corresponding to an m/z mass=361 for all the sera. This signal represents an unknown serum constituent and is used to calibrate the signal intensity. Secondly, a signal is seen on the spectrum of all the above sera at a position representing an m/z ratio=365. The signal corresponds to a hexose dimer as the signal is close to the aforementioned ubiquitous signal it may effectively be used as a standard calibration signal.

Figure 1A:
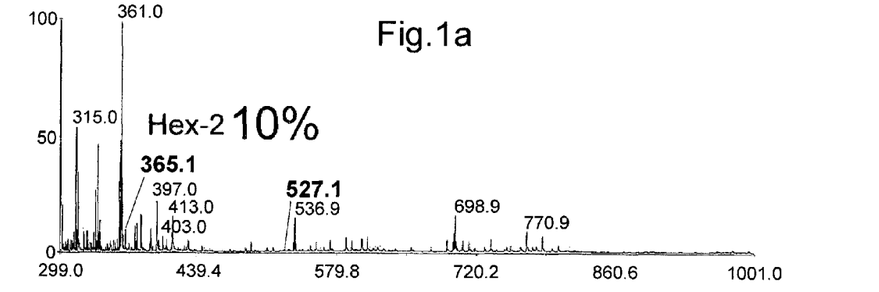
FIG. 1*a* to 1*d* represent, respectively, the mass spectra (MALDI-TOF) obtained according to the method of invention by analysis of MALDI plates prepared from G25, G32, G49 and G48 sera listed in table 1, a compound present in the sample of serum is represented on the spectrum by a peak (or signal) the X axis of the spectrum indicates the m/z ratio (in mass units—MU) of the compound represented by the peak. The Y axis shows the intensity of the signal height (peak height), which corresponds to the amount of compound represented which is contained in the sample, the 100% value being attributed to a ubiquitous, endogenous signal from all sera.
Figure 1B:
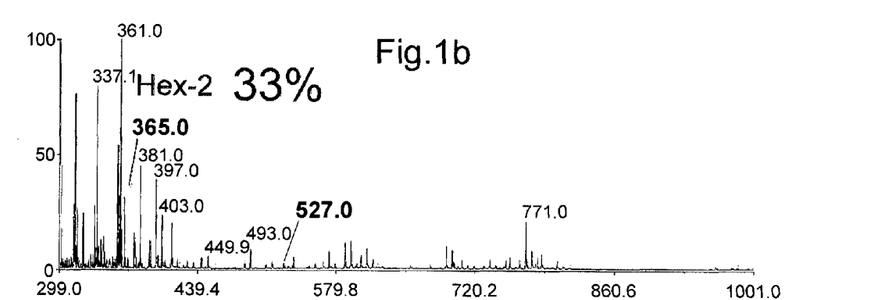
Figure 1C:
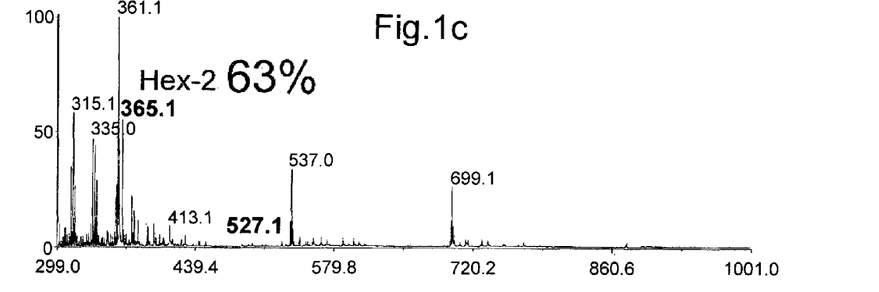
Figure 1D:
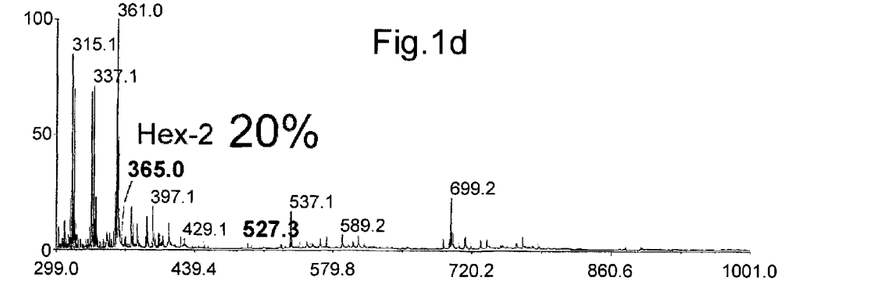
Figure 2A:
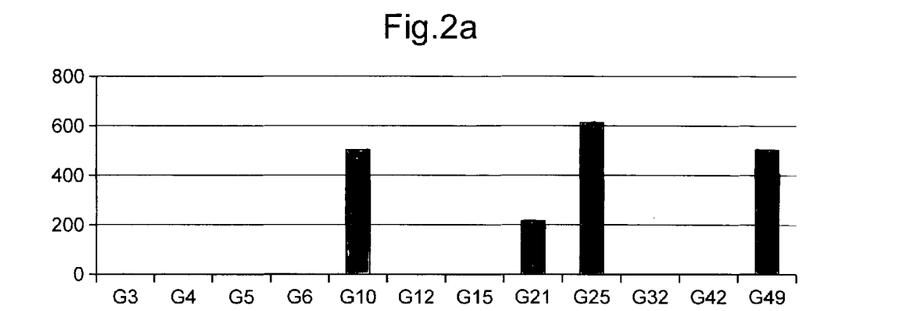
FIG. 2a represents on the vertical axis the amount of mannans (in ng/mL) contained in the samples of sera identified in table 1 and which are showing on the X axis, said quantity being obtained by the use of the Platélia® Candida albicans kit.
Figure 2B:
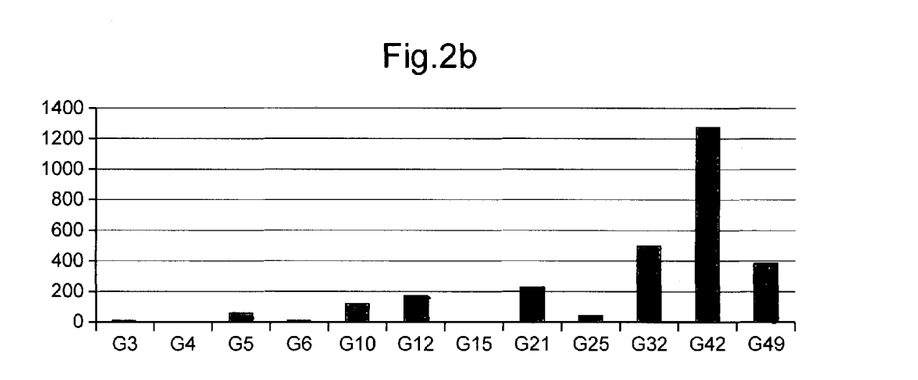
FIG. 2b represents the amount of glucans (in ng/mL) contained in the samples of sera from table 1, the amount of glucans being shown on the Y axis whereas the serum number is shown on the X axis; said amount being measured using the Fungitell® kit.
Figure 2C:
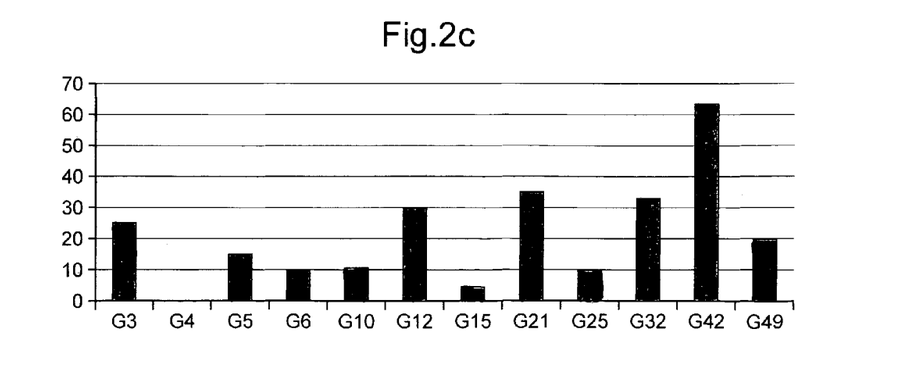
FIG. 2c represents the amount of hexose oligomers (oligomers formed from two hexoses, described in further detail below) contained in each of the samples from table 1. The amount of the aforementioned oligomer in percentage of the ubiquitous signal is shown on the Y axis and the groups on the X axis, said quantity being obtained using the method of the invention and representing the ratio of the peak height obtained from the aforementioned oligomer to the peak height obtained for a ubiquitous signal×100.

In addition, the MALDI plate spectra prepared following the invention method from sera taken from healthy patients (results not shown) do not contain the signal representing an m/z ratio=365, but do contain the ubiquitous symbol as reprinted by an m/z ratio=361. It is therefore possible to deduce that the hexose dimer which is present in sufficient amount to be detectable by MALDI-TOF mass spectrometry originates directly or indirectly from the *Candida albicans* pathogens. FIGS. 2a-2c show the results obtained with commercial kits and the results obtained using the method according to the invention.

Table II below shows the quantitative results obtained from the serum samples applying the invention method. The method according to the invention may be considered to be equivalent to the detection of mannans present in the serum sample and the method for glucans. In other words, the signal corresponding to the aforementioned hexose dimer (m/z=365) can be considered to be at least characteristic to the presence of mannans and glucans in the serum sample concerned. In addition it can be noted that for patients with both glucanaemia and mannanaemia the peak heights corresponding to an m/z=365 to the peak high corresponding to an m/z=361 correlates relatively with the amount of mannans and glucans detected. For serum G4 which was negative with both commercial tests the results were negative according to the invention method (no signal at m/z=365). Conversely, for patients G5, G6 and G15, in whom it was not possible to detect mannans and in which the levels of glucans detected were extremely low or 0, a clear signal representing an m/z ratio=365 is identifiable.

Table II Serum Sample Height of Peak at m/z=365 (height of peak at m/z=361×100)

TABLE II

| Serum sample | (peak height at m/z = 365)/ (peak height at m/z = 361 × 100 |
|---|---|
| G3 | 25 |
| G4 | 0 |
| G5 | 15 |
| G6 | 10 |
| G10 | 11 |
| G12 | 30 |
| G15 | 5 |
| G21 | 35 |
| G25 | 10 |
| G32 | 33 |
| G42 | 63 |
| G49 | 20 |

The invention method can therefore replace both the Platélia® Candida albicans and the Fungitell® tests by detecting substances which are present as indicated by positivity of these tests. In addition, the method according to the invention can detect a signal representing an m/z=365, even in sera which were found not to contain glucans and mannans with the commercial kits. The invention method therefore is more sensitive and more reliable than the aforementioned commercial kits. The results shown were obtained on a MALDI-TOF M/S instrument on the "reflectron" analytical mode; the MALDI-TOF "linear" analytical mode obtains the same result.

Characterisation of the Substance of Interest Producing an m/z=365.

In order to establish the structure of the compound of interest used as a marker for the diagnosis of an invasive fungal infection represented by an m/z peak=365, the supernatant or sera of patients suffering from invasive candidiasis was per-methylated. The sera from patients suffering from invasive candidiasis were therefore treated following stages one and two defined above as a result of the sugars contained in the elute obtained at the second stage and dissolved in water were then permethylated. The permethylation technique is known to the Man skilled in the Art and described in particular in the following publication "Ciucanu I, Kerek F. 1984." A simple and rapid method for the per-methylation of carbohydrates."Carbohydr Res. 131:209-217". MALDI plates are then prepared following the protocol described in the third aforementioned stage [M+Na]$^+$ signal obtained from the per methylated sugar appears at an m/z value=477, which indeed corresponds to a per methylated hexose disaccharide.

The sera from patients suffering from invasive candidiasis processed according to the first two above aforementioned stages, which have undergone per methylation exhibit a chromatographic peak (gas phase chromatography with flame ionisation detector, FID-GC: Alltech ECONO-CAP EC-1, apolar capillary column [30 m×0.25 mm×0.25 um]. Runtime=28.8 min with temperature gradient ranging from 180° C. to 330° C. corresponding to an identical retention time to the retention time to per methylated trehalose (αGlc1-1αGlc). GCEI/MS (Gas phase chromatography coupled to electronic impact mass spectrometry, SGE SolGel-1 ms [30 m×0.25 mm×0.25 μm], identical experimental conditions for those used for GC/FID for sera from patients diagnosed with invasive candidiasis, processed according to the first 30 aforementioned stages, which had undergone per methylation exhibit an IEMS fragmentation spectrum which is identical to that of per methylate trehalose (αGlc1-1αGlc). On this basis, it is concluded that the compound of interest identified by MALDI-TOF mass spectrometry represented by a signal of m/z=365 is a disaccharide, and more specifically trehalose. This compound of interest can therefore be used as a marker for the diagnosis of invasive fungal infection and more specifically for invasive infection caused by C. albicans.

Determination of the Fungal Origin of the Compound of Interest and its Relationship with an Invasive Fungal Infection In Vitro Experiments Mouse neutrophil granulocytes were collected from the abdominal cavity of mice which had received an intraperitoneal injection of thioglycolate following the method as described by Pluskota et al. (J Immunol. 2008 Sep. 1; 181(5): 3609-I9.). Six hours after this injection, the mice were sacrificed by carbon dioxide inhalation and their abdominal cavity was opened. The granulocytes were collected by abdominal cavity lavage, using 5 ml of an iced PBS (phosphate buffered saline) solution.

In order to reduce possible contamination with macrophages, the cells were cultured in petri dishes containing culture tissue covered with foetal calf serum in an incubator at 37° C. in atmosphere containing 5% carbon dioxide for one hour. The non-adherent granulocytes were collected from the supernatant, centrifuged (for 10 min at 2.250 g) counted with a haematimeter and then re suspended in Hank's Balanced Salt Solution (HBSS, marketed by the Invitrogen Company, France). Human granulocytes were isolated from blood cells taken from healthy volunteers, with an acid dextrose citrate solution (1 volume of 154 M citrate and 2 volumes of 2% dextrose, pH=4.6). They were isolated by centrifuging on a Ficoll-Hypaque instrument followed by sedimentation of erythrocytes in dextran and hypotonic lysis of the residual erythrocytes.

Assessment of Destruction of C. albicans by Granulocytes

Yeasts ($10^6$ units) from C. albicans strain SC5314 were suspended in 0.25 ml solution containing 0.1 M HEPES (N-2-hydroxyethylpiperazine-A/-2'-ethanesulfonic acid) pH7 and mixed at 1640 rpm then mixed with $3×10^6$ human granulocytes in a ratio of 1:3. The mixture of granulocytes—yeasts—was incubated at 37° C., mixing gently for one to two hours. Every 30 minutes an aliquot of 300 μL of the mixture was removed and used to detect the presence or absence of the compound of interest corresponding to an m/z=365. The compound of interest was detected by MALDI-TOF mass spectrometry under the same conditions as described above. The signal corresponding to the compound of interest m/z=365 appeared after approximately two hours for both human and murine granulocytes, proving that the compound of interest probably originates from the interaction between C. albicans and the granulocytes which are the mammals' first line of defense cells against fungal pathogens.

In Vivo Experiments in Mice
Animals

Female C57BL/6 six to eight week old mice were used for all the experiments described in the present application. All of the mice were supplied by the Charles River Laboratories (France) and all of the animal experiments were carried out according to protocols approved by the Lille University Regional Hospital Centre Animal Experimentation Ethics Committee and accorded to European Directive 86/609/EEC on the protection of animals used for experimental or other scientific purposes.

Four groups each of 10 mice were formed. All of the groups of mice were raised for 14 days from D1 which was the start date of the experiment. On D=14 all of the mice were killed by dislocating their cervical vertebrae and their blood was collected by cardiac puncture. Serum samples were obtained from these blood samples and stored at −20° C. before being used to detect the compound of interest corresponding to an m/z=365. Group 0 was the control group—i.e. this group contained 10 mice which did not receive any treatments. The mice are not naturally (normally) colonised with $C.$ $albicans$.

Group 1 was the group of which intestinal inflammation was induced by adding 1.5% DSS (dextran sodium sulphate, MW 36-50 kDa; MP Biomedicals, LLC, Germany) in drinking water given from day 1 to day 14. This group was not colonised with $C.$ $albicans$. Mice in group 2 received 200 ml of (QPS) containing $10^7$ units of $C.$ $albicans$ orally on D1. Intestinal inflammation was also induced in the mice in group 2 by adding 1.5% DSS (sodium dextran sulphate, MW 36-50 kDa; MP Biomedicals, LLC, Germany) in drinking water given from D1 to D14. Administration of DSS which causes intestinal inflammation renders the mouse permissive to the growth of large numbers of yeasts in its gastrointestinal tract. This model mimics hospitalised patients extensively colonised with $candida$. These are patients subjected to radio- or chemotherapy, and their intestinal walls are damaged.

The 10 mice in group 3 received an intravenous injection of $10^4$ units of $C.$ $albicans$, strain SC5314 contained in 0.1 ml of sterile saline solution into their tail vein on D1. This group mimics massive candidaemia, causing invasive candidiasis, which is fatal in the mouse and represents candidiaemia (invasive fungal infection) in a hospitalised patient, which is generally fatal if not treated. The presence or absence of mannan in sera from the four groups of mice was tested using the Platélia® Candida albicans kit. Table III below shows the mean measurements of mannans present in the sera of each of the aforementioned groups 0 to 3. Table III mouse groups 0 to 3 mean mannan concentration contained in serum.

TABLE III

| Mouse group | Mean mannan concentration present in serum (pg/mL) |
| --- | --- |
| 0 | <1000 |
| 1 | 2800 |
| 2 | 4200 |
| 3 | 8400 |

The results in Table III prove that the Platélia® $candida$ $albicans$ test was also positive in the case of colonised mice which were not suffering from candidaemia in the mice from group 3.

The presence or absence of the compound of interest corresponding to an m/z=365 was then detected in the sera from the mice in each group. The same experimental protocol was used as above as described for patient sera. No m/z=365 signal representing the compound of interest was detected in the sera from the mice belonging to groups 0, 1 or 2; an m/z=365 signal was only detected by MALDI-TOF mass spectrometry in each of the sera pre-treated following the first two stages of the invention method in the mice in group 3. As a result, the invention method reliably diagnoses invasive fungal infection and distinguishes invasive fungal infection from massive colonisation of the gastrointestinal tract, which is not the case for the aforementioned commercial kits.

What is claimed is:

1. An in vitro method for the diagnosis of a fungal infection caused by a pathogenic fungal microorganism, comprising:
   extracting a sample containing complexes from a biological liquid obtained from a human or mammal, containing at least one of trehalose and hydrolytic precursors of trehalose complexed with at least one of proteins, lipids, and salts;
   using MALDI-TOF mass spectrometry to detect presence of at least one standard compound added to a positive control, and to establish the presence or absence of at least trehalose in said sample;
   determining, based on said established presence or absence of at least trehalose in said sample and further in dependence on said MALDI-TOF mass spectrometry of said positive control, that if said at least trehalose is present in said sample, the human or mammal is suffering from the fungal infection.

2. The method according to claim 1, wherein in order to extract said at least one of trehalose and hydrolytic precursors of trehalose in said sample,
   said complexes contained in said sample are separated from the biological liquid by at least one of precipitation and coagulation of a majority of at least one of proteins and lipids in the sample;
   said sample is centrifuged and a supernatant is separated from a solid phase;
   said supernatant is recovered; and
   said at least one of trehalose and hydrolytic precursors of trehalose contained in the supernatant are separated from any residual proteins and any residual lipids by a first chromatographic process, and said at least one of trehalose and hydrolytic precursors of trehalose are separated from said salts by a second chromatographic process.

3. The method according to claim 2, wherein in order to separate said complexes from the biological liquid, EDTA as a complexing agent is added and the resulting mixture is heated to a temperature of between 100° C. and 140° C.

4. The method according to claim 2, wherein the first chromatographic process comprises reverse phase chromatography, the second chromatographic process comprises absorption chromatography, and the second chromatographic process follows the first chromatographic process.

5. The method according to claim 4, wherein a column containing a hydrophobic phase is used for the reverse phase chromatography and a column containing activated charcoal is used for the absorption chromatography.

6. The method according to claim 1, wherein said at least one of trehalose and hydrolytic precursors of trehalose has an m/z ratio of under 1000.

7. The method according to claim 1, further comprising adding at least one lytic enzyme adapted to act on said complexes to cleave chains of at least one of polysaccharides and oligosaccharides which are lytic enzyme substrates, and result in an increased amount of trehalose in said sample.

8. The method according to claim 1, wherein said hydrolytic precursors of trehalose are selected from the group consisting of oligosaccharides containing 2 to 10 sugars.

9. The method according to claim 7, wherein said at least trehalose and hydrolytic precursors of trehalose produced by said pathogenic fungal microorganism.

10. The method according to claim 1, wherein said pathogenic fungal microorganism is selected from the group consisting of
Candida spp.,
Aspergillus spp.,
Fusarium spp.,
Trichosporon spp.,
Saccharomyces cerevisiae,
Acremonium spp.,
Scedosporium spp.,
Coccidioides immitis,
Histoplasma capsulatum,
Sporothrix schenckii, and
Pneumocystis jirovecii.

11. The method according to claim 1, wherein said positive control is prepared by adding a known amount of the at least one standard compound to at least a portion of said sample in order that by comparing an intensity of a mass spectrographic signal obtained for said at least trehalose with a signal obtained for said positive control containing said at least one standard compound, an amount of said at least trehalose contained in said sample can be established.

12. The method according to claim 1, wherein a ratio of an intensity of a mass spectrographic signal corresponding to the at least trehalose to an intensity of an endogenous signal is determined, said intensity of the endogenous signal being predetermined.

13. The method according to claim 1, wherein said biological liquid is selected from the group consisting of: venous and arterial blood, serum, genital mucosal liquids, respiratory tract liquids, liquid from bronchial alveolar lavage, bronchial aspiration, tracheal aspiration, expectoration, sputum, liquids used to collect skin and integument fractions, effusion liquids, liquids from closed cavities, cerebrospinal liquid, gastrointestinal tract liquids, urinary liquids, and liquids obtained from grinding a biopsy fragment.

14. A method for diagnosing a fungal infection of a human or animal, comprising:
obtaining a biological sample containing characteristic fungal carbohydrate metabolites from the human or animal;
extracting complexes from the biological sample of the characteristic fungal carbohydrate metabolites with at least one of proteins, lipids, carbohydrates, and salts;
subjecting at least the extracted complexes or enzymatic degradation products of the extracted complexes to MALDI-TOF mass spectrometry;
analyzing a resulting mass spectrogram to determine an amount of characteristic fungal carbohydrate metabolites comprising trehalose present in the biological sample; and
producing an output signal corresponding to, or dependent upon, the amount of characteristic fungal carbohydrate metabolites comprising trehalose present in the biological sample, wherein the output signal is further dependent on at least a positive control.

15. The method according to claim 14, further comprising treating at least a portion of the biological sample with at least one mannosidase, adapted to alter an amount of the characteristic fungal carbohydrate metabolites by action on mannans of fungal origin.

16. The method according to claim 14, further comprising treating at least a portion of the biological sample with at least one galactomannosidase, to alter an amount of the characteristic fungal carbohydrate metabolites by action on galactomannans of fungal origin.

17. The method according to claim 14, further comprising treating at least a portion of the biological sample with at least one glucanase, adapted to alter an amount of the characteristic fungal carbohydrate metabolites by action on glycosides of fungal origin.

18. The method according to claim 14, further comprising treating at least a portion of the biological sample with at least one chitinase, adapted to decrease an amount of the characteristic fungal carbohydrate metabolites by action on chitin of fungal origin.

19. The method according to claim 14, wherein the positive control comprises a known amount of an isotope tracer for the characteristic fungal carbohydrate metabolites added to the biological sample prior to extracting and MALDI-TOF mass spectrometry, to thereby provide a quantitative internal standard.

* * * * *